United States Patent

Eierdanz et al.

Patent Number: 5,650,158
Date of Patent: Jul. 22, 1997

[54] SKIN-CONDITIONING SUCCINIC ACID DERIVATIVES

[75] Inventors: Horst Eierdanz, Hilden; Peter Busch, Erkrath; Holger Tesmann, Juechen; Walter Knoerr, Hilden; Rolf Wachter, Duesseldorf, all of Germany

[73] Assignee: Henkel Kommanditgesellschaft auf Aktien, Duesseldorf, Germany

[21] Appl. No.: 433,483

[22] PCT Filed: Nov. 2, 1993

[86] PCT No.: PCT/EP93/03044

§ 371 Date: May 11, 1995

§ 102(e) Date: May 11, 1995

[87] PCT Pub. No.: WO94/11333

PCT Pub. Date: May 26, 1994

[30] Foreign Application Priority Data

Nov. 11, 1992 [DE] Germany ............... 42 38 032.4

[51] Int. Cl.$^6$ ............................................. A61K 7/48
[52] U.S. Cl. ............... 424/401; 424/43; 424/59; 424/101; 514/844; 514/937; 514/938; 560/198; 560/199
[58] Field of Search ............... 424/401, 701, 424/59, 43; 514/844, 937, 938; 560/198, 199

[56] References Cited

U.S. PATENT DOCUMENTS

3,968,310  7/1976  Stowell ............... 428/411

FOREIGN PATENT DOCUMENTS

0107199  5/1984  European Pat. Off. .
0277641  8/1988  European Pat. Off. .
0455429  11/1991  European Pat. Off. .

OTHER PUBLICATIONS

J. Soc. Cosmet. Chem. 40 (1989), 273–285.

Primary Examiner—Jyothsna Venkat
Attorney, Agent, or Firm—Ernest G. Szoke; Wayne C. Jaeschke; Real J. Grandmaison

[57] ABSTRACT

A skin-moisture-regulating composition for cosmetic or dermatological preparations, the composition containing succinic acid derivatives corresponding to formula I:

$$R^1O(C_nH_{2n}O)_xCO\text{—}CHR^2\text{—}CHR^3\text{—}CO(OC_nH_{2n}O)_yOR^4 \quad (I)$$

wherein $R^1$ is an alkyl, alkenyl, mono-or dihydroxyalkyl or hydroxyalkenyl group containing 6 to 22 carbon atoms, one of $R^2$ and $R^3$ is hydrogen and the other is an alkyl or alkenyl group containing 12 to 22 carbon atoms, n=2 or 3, x and y are average degrees of alkoxylation and have values of 0 to 20 and 1 to 20, respectively, and $R^4$ is hydrogen or a group $R^1O\text{—}(C_nH_{2n}O)_x\text{—}CO\text{—}CHR^2\text{—}CHR^3\text{—}CO\text{—}$, or an alkyl, alkenyl, mono- or dihydroxyalkyl or hydroxyalkenyl group containing 6 to 22 carbon atoms.

19 Claims, No Drawings

SKIN-CONDITIONING SUCCINIC ACID DERIVATIVES

BACKGROUND OF THE INVENTION

1. Field of the Invention

This invention relates to new succinic acid derivatives with a lipid-like structure which are suitable as a skin-moisture-regulating component in cosmetic and dermatological preparations.

Keeping the skin healthy and promoting a cosmetically attractive smooth appearance and a soft feel means, above all, maintaining the natural moisture content of the stratum corneum. There are many known skin-moisturizing and moisture-retaining additives for cosmetic and therapeutic skin treatment compositions. They are generally water-soluble or water-binding substances or even hygroscopic compounds. Most of these substances have the disadvantage that, in the event of frequent use, they contribute towards even greater drying out of the skin.

Paraffin oils, triglyceride oils and waxes are distinguished by an excessively occlusive effect which seriously inhibits the transepidermal exchange of water.

2. Discussion of Related Art

The stratum corneum lipids of the human skin and also synthetic analogs of these lipids have recently become known for their effectiveness in regulating skin moisture (J. Soc. Cosmet. Chem. 40 (1989), 273–285). The synthetic lipid analogs in question are, for example, N-acyl sphingosines and fatty acid amides of 1-N-hydroxy-ethylamino-2-hydroxy-3-alkoxypropane (cf. for example EP 0 277 641, EP 0 455 429).

DESCRIPTION OF THE INVENTION

It has now been found that alkyl and alkenyl succinic acid monoester alkoxylates, which are easy to synthesize, are also analogous in their effect to the natural and synthetic ceramides.

The present invention relates to succinic acid derivatives corresponding to formula I:

$$R^1O(C_nH_{2n}O)_xCO\text{—}CHR^2\text{—}CHR^3\text{—}CO(OC_nH_{2n}O)_yOR^4 \quad (I)$$

in which $R^1$ is an alkyl, alkenyl, mono- or dihydroxyalkyl or hydroxyalkenyl group containing 6 to 22 carbon atoms, one of the substituents $R^2$ and $R^3$ is hydrogen and the other is an alkyl or alkenyl group containing 12 to 22 carbon atoms, n=2 or 3, x and y are average degrees of alkoxylation and have values of 0 to 20 and 1 to 20, respectively, and $R^4$ is hydrogen or a group $R^1O\text{—}(C_nH_{2n}O)_x\text{—}CO\text{—}CHR^2\text{—}CHR^3\text{—}CO\text{—}$ or has the same meaning as $R^1$.

The succinic acid derivatives according to the invention are eminently suitable for use as a skin-moisture-regulating component for the production of cosmetic or therapeutic skin treatment preparations. By virtue of their lipid character, they increase the smoothness and softness of the skin and regulate the transepidermal loss of water without forming a water-impermeable barrier. They prevent the skin from drying out under the effect of climate and surfactants and contribute towards the skin retaining a smooth and youthful appearance.

The succinic acid derivatives according to the invention are prepared by methods known per se in preparative chemistry from the known alkenyl succinic anhydrides which can be obtained by ene addition of maleic anhydride onto olefins. A corresponding succinic anhydride of general formula II:

in which one of the substituents $R^2$ and $R^3$ is hydrogen and the other is an alkenyl group containing 12 to 22 carbon atoms, is reacted with an alcohol of the formula $R^1\text{—OH}$ to form the monoester and the monoester is then alkoxylated with (x+y) moles of ethylene oxide (n=2) or propylene oxide (n=3). $R^1$, $R^2$, $R^3$, n, x and y have the same meanings as in formula I. If the substituent $R^2$ or $R^3$ is to be an alkyl group, the succinic anhydride corresponding to formula II, the monoester or the alkoxylate may be hydrogenated to saturate the double bonds present.

Suitable alcohols $R^1OH$ are, for example, fatty alcohols containing 6 to 22 carbon atoms, preferably for example stearyl, arachidyl, behenyl, oleyl, linoleyl and erucic alcohol. Alkanediols and alkanetriols containing 6 to 22 carbon atoms, for example ricinolyl alcohol, 9-hydroxystearyl alcohol, and alkanetriols, such as 9,10-dihydroxystearyl alcohol for example, are also suitable.

The alkoxylation of the monoester is preferably carried out in the presence of basic catalysts, such as for example LiOH, NaOH, KOH, $NaOCH_3$, $KOCH_3$ and other known catalysts for the reaction of ethylene oxide or propylene oxide with reactive hydroxyl groups. The alkoxylation reaction is preferably carried out at temperatures of 100° to 200° C., under a slight excess pressure of 1 to 10 bar and with an excess of ethylene or propylene oxide. The monoester corresponding to formula I adds a first mole of alkylene oxide onto the free carboxyl group (y=1), even in the absence of a catalyst. If it is desired to add more than 1 mole of alkylene oxide, a second alkoxylation step has to be carried out in the presence of an alkoxylation catalyst or, alternatively, the alkoxylation reaction should be carried out from the outset in the presence of a catalyst.

Where the alkoxylation reaction is carried out in the presence of a catalyst, alkylene oxide is also introduced into the ester bond of the monoester; the alkoxy groups x in formula I are added in this way. Finally, the alkoxylation is also accompanied by partial transesterification of the alkoxylate corresponding to formula I with $R^4$=H to form complex esters in which $R^4=R^1O(C_nH_{2n}O)_x\text{—}CO\text{—}CHR_2\text{—}CHR^3\text{—}CO\text{—}$ or has the same meaning as $R^1$. However, monoester ethoxylates corresponding to formula I, in which $R^4$=H, are the main component of the reaction mixture.

Alternatively, the monoester nay also be converted into the alkali metal or alkaline earth metal salt which is then alkoxylated in an inert solvent.

Among the succinic acid derivatives of formula I according to the invention, those in which $R^1$ is an alkyl group containing 16 to 22 carbon atoms and more particularly 20 to 22 carbon atoms are preferred as a skin-moisture-regulating lipid component for the production of cosmetic and therapeutic skin treatment preparations. Succinic acid derivatives corresponding to formula I in which n=2 and (x+y)=1 to 20 are particularly preferred.

The new compounds are oil-soluble and show a certain interfacial activity by virtue of the polar groups in the molecule. Accordingly, they are particularly easy to incorporate in cosmetic and dermatological formulations. The succinic acid derivatives according to the invention are preferably incorporated in a suitable cosmetic or dermatological carrier in a quantity of 1 to 10% by weight.

Suitable carriers are both cosmetic oils and aerosol preparations and also aqueous emulsion-like systems. They form clear solutions in typical oil components, for example in paraffin oil, vegetable oils and fatty acid esters. They may be emulsified with water both individually and in admixture with typical cosmetic oil components using known emulsifiers, oil-in-water emulsions, water-in-oil emulsions or mixed emulsion systems being obtained according to the emulsifier and the emulsifying method used. The succinic acid derivatives according to the invention may thus readily be incorporated, for example, in skin creams, lotions, skin oils, sunscreen preparations, body aerosols, hair lotions and bath oils.

The following Examples are intended to illustrate the invention.

EXAMPLES

1. Preparation Examples 1.1 Hexadecenyl succinic acid monoerucyl ester ethoxylate (4.5 EO) ($R^1$=erucyl, $R^2$=H, $R^3$=hexadecenyl, n=2, (x+y) =4.5)

551 g (1.7 moles) of hexadecenyl succinic anhydride (short-path-distilled) were stirred with 649.2 g (2 moles) of erucic alcohol for 0.5 h at 60° C. Characteristic data: AV (acid value) 83, OHV (OH value) 18, SV (saponification value) 153, IV (iodine value) 78.

2-Stage Ethoxylation of the Monoester 500 g (0.77 mole) of the monoester were stirred with 211.6 g (4.8 moles) of ethylene oxide for 8 h at 180° C./5 bar ($N_2$).

Yield: 535.9 g of a yellow viscous liquid

Approximately 1 mole of EO was taken up per mole of semiester.

Characteristic data: AV 3.2

1.2 g (30% in methanol) of sodium methylate were added to 232.3 g of pre-ethoxylated semiester (0.33 mole), followed by ethoxylation with 84.1 g (1.9 mole) of ethylene oxide for 2 h at 150° C./5 bar ($N_2$). The dark-colored crude product is filtered through Tonsil/ active carbon.

Yield: 291.4 g of a light yellow viscous liquid.

Approximately 3.6 moles of EO were additionally taken up per mole of semiester ethoxylate.

The total degree of ethoxylation is 4.5 moles of EO per mole of semiester.

Characteristic data: AV 0.4, OHV 44, IV 53, SV 100

1.2 Hexadecyl succinic acid monostearyl ester ethoxylate (7.6 EO) ($R^1$=stearyl, $R^2$=H, $R^3$=hexadecyl, n=2, (x+y)= 7.6)

275.7 g (0.85 mole) of hexadecenyl succinic anhydride (short-path-distilled) were stirred for 1 h at 80° C. with 297.6 g (1.1 mole) of stearyl alcohol. A light yellow solid is obtained.

Characteristic data: AV 79, OHV 16.5, SV 166, AV 36

Hydrogenation 529.4 g (0.9 mole) of monostearyl ester were hydrogenated for 3 h at 80° C./10 bar $H_2$ on 26.5 g of palladium on active carbon (5% Pd) until no more hydrogen was taken up. Filtration through Hyflo gives 409.6 g of a light yellow solid. characteristic data: IV 0.3

Ethoxylation of the Hydrogenated Ester 379.4 g (0.64 mole) of the hydrogenated monoester were stirred for 8 h at 180° C./5 bar ($N_2$) with 1.9 g (12 mole-%) of LiOH and 250.4 g (5.7 moles) of ethylene oxide. The crude product was stirred with 2% (based on the mixture as a whole) of Tonsil for 1 h at 90° C. and then filtered through Hyflo.

Yield: 617.5 g of a yellow solid

Approximately 7.6 moles of EO were taken up per mole of semiester.

Characteristic data: AV 0.8, OHV 78, SV 94

1.3 Hexadecyl succinic acid monobehenyl ester ethoxylate (7.3 EO) ($R^1$=behenyl, $R^2$=H, $R^3$=hexadecyl, n=2, (x+y) =7.3)

275.7 g (0.85 mole) of hexadecenyl succinic anhydride (short-path-distilled) were stirred with 359.3 g (1.1 mole) of behenyl alcohol (Stenol 1822 A) for 1 h at 80° C.

Characteristic data: AV 74, OHV 11.7, SV 152, IV 30

Hydrogenation 529.4 g (0.8 mole) of monobehenyl ester were hydrogenated on 26.5 g of palladium on active carbon (5% Pd) for 3 h at 80° C./10 bar $H_2$ until no more hydrogen was taken up. Filtration through Hyflo gives 431.8 g of a light yellow solid.

Characteristic data: IV 1.0

Ethoxylation of the Hydrogenated Ester 394.8 g (0.6 mole) of the hydrogenated monoester were stirred with 2 g (12 mole-%) of LiOH and 229.3 g (5.2 moles) of ethylene oxide for 10 h at 180° C./5 bar ($N_2$). The crude product was stirred with 2% (based on the mixture as a whole) of Tonsil for 1 h at 90° C. and then filtered through Hyflo.

Yield: 604.4 g of a yellow solid.

Approximately 7.3 moles of EO were taken up per mole of semiester.

Characteristic data: AV 0.4, OHV 73, SV 92

1.4 Hexadecyl succinic acid monostearyl ester ethoxylate (1.3 EO) ($R^1$=stearyl, $R^2$=H, $R^3$=hexadecyl, n=2, (x+y)= 1.3)

275.5 g (0.85 mole) of hexadecenyl succinic anhydride (short-path-distilled) were stirred with 297.6 g (1.1 mole) of stearyl alcohol for 1 h at 80° C. A light yellow solid is obtained.

Characteristic data: AV 84, OHV 20, SV 167, IV 37

Ethoxylation of the Semiester 382.2 g (0.65 mole) of the monoester were stirred with 2.1 g (12 mole-%) of LiOH and 46.2 g (1.05 mole) of ethylene oxide for 5 h at 180° C./5 bar ($N_2$). The crude product was stirred with 2% (based on the mixture as a whole) of Tonsil for 1 h at 90° C. and then filtered through Hyflo.

Yield: 423.6 g of a yellow solid

Approximately 1.3 moles of EO were taken up per mole of semiester.

Characteristic data: AV 0.5, OHV 89, SV 143, IV 33

Hydrogenation 200 g (0.3 mole) of monostearyl ester ethoxylate were hydrogenated on 1 g of palladium on active carbon (5% Pd) for 3 h at 80° C./10 bar $H_2$ until no more hydrogen was taken up. Filtration through Hyflo gives 161 g of a light yellow solid.

Characteristic data: IV 3.3

The product is distinctly lighter than in Example 1.3.

1.5 Hexadecyl succinic acid monobehenyl ester ethoxylate (7.5 EO) ($R^1$=behenyl, $R^2$=H, $R^3$=hexadecyl, n=2, (x+y) =7.5

Hydrogenation of the Hexadecenyl Succinic Anhydride 300 g (0.93 mole) of hexadecenyl succinic anhydride (distilled) were hydrogenated with 6 g of Ni catalyst (22% of Ni on a support in a fatty matrix) for 4 h at 180° C./10 bar $H_2$ until no more hydrogen was taken up. Filtration through Hyflo gives 280 g of a light yellow solid.

Characteristic data: IV 2.9

Alcoholysis of the Hydrogenated Anhydride With Subsequent Ethoxylation of the Semiester 261 g (0.8 mole) of hexadecyl succinic anhydride were stirred with 271 g (0.84 mole) of behenyl alcohol (Stenol 1822A) under nitrogen for 30 minutes at 80° C. 2.7 g (0.5% by weight) of powdered KOH were added to the reaction product, after which 284 g (6.45 moles) of ethylene oxide were introduced in portions over a period of about 80 minutes at 140° C./4.5 bar ($N_2$) and the whole was reacted for 1 h at 140° C. The crude product was stirred with 2% (based on the mixture as a whole) of Tonsil/active carbon (3:1 w/w) under nitrogen for 1 h at 90° C. and filtered through Hyflo at a maximum temperature of 60° C.

Yield: 777 g of a yellow solid

Approximately 7.5 moles of EO were taken up per mole of semiester.

Characteristic data: AV 0.3, OHV 64, SV 111

2. Application Examples 2.1 O/w Hand-care Cream

Cutina CBS[1] 12.0% by weight
Decyl oleate 6.0% by weight
Succinic acid derivative of Example 1.3 6.0% by weight
Paraffin oil, low-viscosity 4.0% by weight
PEG 20 cetyl/stearyl ether 0.5% by weight
PEG 24 glyceryl stearate 2.0% by weight
Glycerol 5.0% by weight
Almond protein hydrolyzate 5.0% by weight
Preservative (for example formaldehyde, 30%) 0.15% by weight
Water ad 100% by weight 2.2 P/w Soft Cream Emulgade SE[2] 7.0% by weight
Cetyl/stearyl alcohol 2.0% by weight
2-Octyl dodecanol 3.0% by weight
Decyl oleate 2.0% by weight
Succinic acid derivative of Example 1.3 2.0% by weight
Silicone oil (350 cst) 0.5% by weight
Paraffin oil, high-viscosity 4.0% by weight
Glycerol (86%) 3.0% by weight
Preservative 0.15% by weight
Water ad 100% by weight 2.3 O/w Nutrient and Care Cream Palmitic/stearic acid (65:35) 2.0% by weight
Cutina CBS[1] 6.0% by weight
2-Octyl dodecanol 7.0% by weight
Succinic acid derivative of Example 1.3 7.0% by weight
Paraffin oil, low-viscosity 4.0% by weight
Glycerol (86%) 5.0% by weight
Potassium hydroxide (20% in $H_2O$) 2.0% by weight
Keratin hydrolyzate (20% in $H_2O$) 5.0% by weight
Preservative 0.15% by weight
Water ad 100% by weight 2.4 O/w Skin Cream Glycerol mono-/dipalmitate/stearate 6.0% by weight
PEG 12 cetyl/stearyl ether 1.0% by weight
PEG 20 cetyl/stearyl ether 1.0% by weight
Cetyl/stearyl alcohol 2.0% by weight
Succinic acid derivative of Example 1.3 6.0% by weight
Decyl oleate 3.0% by weight
Cetyl/stearyl isononanoate 3.0% by weight
Paraffin oil, high-viscosity 4.0% by weight
Glycerol, 86% 5.0% by weight
Preservative 0.15% by weight
Water ad 100% by weight 2.5 O/w Skin Cream Glycerol mono-/dipalmitate/stearate 14.0% by weight
Sorbitan monolaurate 2.5% by weight
PEG 20 sorbitan monolaurate 1.5% by weight
2-Octyl dodecanol 5.0% by weight
Dibutyl adipate 5.0% by weight
Succinic acid derivative of Example 1.3 2.0% by weight
Cetyl/stearyl alcohol 1.0% by weight
Glycerol (86%) 3.0% by weight
Preservative 0.15% by weight
Water ad 100% by weight 2.6 O/w Sun Cream Emulgate CBN[3] 12.0% by weight
Cetyl/stearyl alcohol 1.2% by weight
Decyl oleate 2.0% by weight
Succinic acid derivative of Example 1.3 5.0% by weight
Silicone oil (350 cst) 0.5% by weight
Tocopherol (natural) 3.0% by weight
Parsol MCX[4] 7.5% by weight
Parsol 1789[5] 3.0% by weight
Glycerol 86% 3.0% by weight
Preservative 0.15% by weight
Water ad 100% by weight 2.7 W/o Care Cream Caprylic/capric acid triglyceride 11.0% by weight
Paraffin oil, high-viscosity 8.0% by weight
Beeswax 6.0% by weight
Polyglyceryl (3) diisostearate 4.0% by weight
PEG 7 hydr. castor oil ether 2.0% by weight
Succinic acid derivative of Example 1.3 5.0% by weight
Glycerol (86%) 5.0% by weight
$MgSO_4 \cdot 7H_2O$ 0.7% by weight
Preservative 0.15% by weight
Water ad 100% by weight 2.8 W/o Night Cream Polyglyceryl (3) diisostearate 4.0% by weight
PEG 7 hydr. castor oil ether 3.0% by weight
Cetyl/stearyl alcohol 1.0% by weight
Beeswax 5.0% by weight
Zinc stearate 0.5% by weight
Paraffin oil, low-viscosity 7.0% by weight
1,3-bis-(2-ethylhexyl)-cyclohexane 6.0% by weight
Succinic acid derivative of Example 1.3 10.0% by weight
Glycerol (86%) 5.0% by weight
$MgSO_4 \cdot 7H_2O$ 0.7% by weight
Almond protein hydrolyzate (22% in $H_2O$) 2.5% by weight
Preservative 0.15% by weight
Water ad 100% by weight 2.9 W/o Care Lotion PEG 7 hydr. castor oil ether 8.0% by weight
Succinic acid derivative of Example 1.3 8.0% by weight Decyl oleate 5.0% by weight
Cetyl/stearyl isononanoate 5.0% by weight
Zinc stearate 2.0% by weight
Tocopherol 0.5% by weight
Glycerol (86%) 5.0% by weight
MgSO$_4$·7H$_2$O 0.5% by weight
Almond protein hydrolyzate (22% in H$_2$O) 5.0% by weight
Preservative 0.15% by weight
Water ad 100% by weight The following commercial products were used:

(1) Cutina CBS: a mixture of glycerol mono-/dipalmitate/stearate cetyl/stearyl alcohol cetyl palmitate cocofatty acid triglyceride (2) Emulgade SE: a mixture of glycerol mono-/dipalmitate/stearate cetyl/stearyl alcohol PEG 20 cetyl/stearyl ether PEG 12 cetyl/stearyl ether cetyl/stearyl alcohol cetyl palmitate (3) Emulgade CNB: a mixture of cetyl/stearyl isononanoate glycerol mono-/dipalmitate/stearate PEG 20 glycerol monostearate cetyl/stearyl alcohol PEG 20 cetyl/stearyl ether cetyl palmitate (4) Parsol MCX: 4-methoxycinnamic acid-2-ethyl hexyl ester (5) Parsol 1789: 4-tert.butyl-4'-methoxydibenzoyl methane

We claim:

1. A skin-moisture-regulating composition present in cosmetic or dermatological preparations, said composition comprising succinic acid derivatives corresponding to formula I:

wherein $R^1$ is an alkyl, alkenyl, mono-or dihydroxyalkyl or hydroxyalkenyl group having 6 to 22 carbon atoms, one of $R^2$ and $R^3$ is hydrogen and the other is an alkyl or alkenyl group having 12 to 22 carbon atoms, n=2 or 3, x and y are average degrees of alkoxylation and have values of 0 to 20 and 1 to 20, respectively, and $R^4$ is hydrogen or a group $R^1O-(C_nH_{2n}O)_x-CO-CHR^2-CHR^3CO-$, or an alkyl, alkenyl, mono- or dihydroxyalkyl or hydroxyalkenyl group having 6 to 22 carbon atoms.

2. The composition of claim 1 wherein $R^1$ is an alkyl group having 16 to 22 carbon atoms.

3. The composition of claim 1 wherein n=2, and (x+y)=1 to 20.

4. The composition of claim 1 present in said cosmetic or dermatological preparations in an amount of from 1 to 10% by weight, based on the weight of said preparation.

5. The composition of claim 1 wherein said composition is oil-soluble.

6. The composition of claim 1 present in cosmetic or dermatological preparations selected from the group consisting of skin cream, lotion, skin oil, sunscreen, body aerosol, hair lotion and bath oil.

7. A process for treating human skin comprising contacting said skin with a cosmetic or dermatological preparation containing a composition comprising succinic acid derivatives corresponding to formula I:

wherein $R^1$ is an alkyl, alkenyl, mono-or dihydroxyalkyl or hydroxyalkenyl group having 6 to 22 carbon atoms, one of $R^2$ and $R^3$ is hydrogen and the other is an alkyl or alkenyl group having 12 to 22 carbon atoms, n=2 or 3, x and y are average degrees of alkoxylation and have values of 0 to 20 and 1 to 20, respectively, and $R^4$ is hydrogen or a group $R^1O-(C_nH_{2n}O)_x-CO-CHR^2-CHR^3-CO-$, or an alkyl, alkenyl, mono- or dihydroxyalkyl or hydroxyalkenyl group having 6 to 22 carbon atoms.

8. The process of claim 7 wherein $R^1$ is an alkyl group having 16 to 22 carbon atoms.

9. The process of claim 7 wherein n=2, and (x+y)=1 to 20.

10. The process of claim 7 wherein said composition is present in said cosmetic or dermatological preparation in an amount of from 1 to 10% by weight, based on the weight of said preparation.

11. The process of claim 7 wherein said composition is oil-soluble.

12. The process of claim 7 wherein said cosmetic or dermatological preparation is selected from the group consisting of skin cream, lotion, skin oil, sunscreen, body aerosol, hair lotion and bath oil.

13. A process for formulating a cosmetic or dermatological preparation comprising adding to said preparation a skin-moisturizing effective amount of a composition comprising succinic acid derivatives corresponding to formula I:

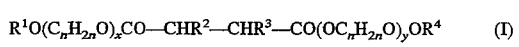

wherein $R^1$ is an alkyl, alkenyl, mono-or dihydroxyalkyl or hydroxyalkenyl group having 6 to 22 carbon atoms, one of $R^2$ and $R^3$ is hydrogen and the other is an alkyl or alkenyl group having 12 to 22 carbon atoms, n=2 or 3, x and y are average degrees of alkoxylation and have values of 0 to 20 and 1 to 20, respectively, and $R^4$ is hydrogen or a group $R^1O-(C_nH_{2n}O)_x-CO-CHR^2-CHR^3-CO-$, or an alkyl, alkenyl, mono- or dihydroxyalkyl or hydroxyalkenyl group having 6 to 22 carbon atoms.

14. The process of claim 13 wherein $R^1$ is an alkyl group having 16 to 22 carbon atoms.

15. The process of claim 13 wherein n=2, and (x+y)=1 to 20.

16. The process of claim 13 wherein from 1 to 10% by weight of said composition is added to said cosmetic or dermatological preparation, based on the weight of said preparation.

17. The process of claim 13 wherein said composition is oil-soluble.

18. The process of claim 13 wherein said cosmetic or dermatological preparation is selected from the group consisting of skin cream, lotion, skin oil, sunscreen, body aerosol, hair lotion and bath oil.

19. A process for preparing succinic acid derivatives corresponding to formula I:

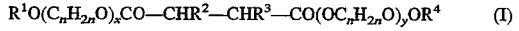

wherein $R^1$ is an alkyl, alkenyl, mono-or dihydroxyalkyl or hydroxyalkenyl group having 6 to 22 carbon atoms, one of $R^2$ and $R^3$ is hydrogen and the other is an alkyl or alkenyl group having 12 to 22 carbon atoms, n=2 or 3, x and y are average degrees of alkoxylation and have values of 0 to 20 and 1 to 20, respectively, and $R^4$ is hydrogen or a group $R^1O-(C_nH_{2n}O)_x-CO-CHR^2-CHR^3-CO-$, or an alkyl, alkenyl, mono- or dihydroxyalkyl or hydroxyalkenyl group having 6 to 22 carbon atoms, comprising reacting a succinic anhydride corresponding to formula (II):

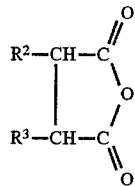
(II)

in which one of the substituents $R^2$ and $R^3$ is hydrogen and the other is an alkenyl group having 12 to 22 carbon atoms, with an alcohol having the formula $R^1$—OH to form the monoester, adding (x+y) moles of ethylene oxide or propylene oxide to the monoester wherein the monoester or the alkoxylate is optionally hydrogenated to saturate the double bonds present.

* * * * *